US00PP20175P2

(12) United States Plant Patent
Meilland

(10) Patent No.: US PP20,175 P2
(45) Date of Patent: Jul. 7, 2009

(54) SHRUB ROSE PLANT NAMED 'MEIZMEA'

(50) Latin Name: *Rosa hybrida*
Varietal Denomination: Meizmea

(75) Inventor: Alain A. Meilland, Antibes (FR)

(73) Assignee: CP Delaware, Inc., Wilmington, DE (US)

( * ) Notice: Subject to any disclaimer, the term of this patent is extended or adjusted under 35 U.S.C. 154(b) by 0 days.

(21) Appl. No.: 12/213,555

(22) Filed: Jun. 20, 2008

(51) Int. Cl.
*A01H 5/00* (2006.01)

(52) U.S. Cl. ..... Plt./107
(58) Field of Classification Search ..... Plt./107
See application file for complete search history.

*Primary Examiner*—Annette H Para
(74) *Attorney, Agent, or Firm*—Buchanan Ingersoll & Rooney PC

(57) ABSTRACT

A new and distinct variety of Shrub Rose plant is provided that abundantly forms attractive small single cup-shaped blossoms that are bright red with a light pink center on the upper surface. A bushy and compact growth habit is displayed and the foliage is semi-glossy. The disease tolerance is very good particularly with respect to Black Spot and Oidium. The plant is well suited for providing attractive ornamentation in the landscape, such as in parks and gardens.

1 Drawing Sheet

Figures 1, 2, 3, 4, 5, 6, 7, 8, 9, 10, 11, 12, 13, 14, 15, 16, 17, 18:
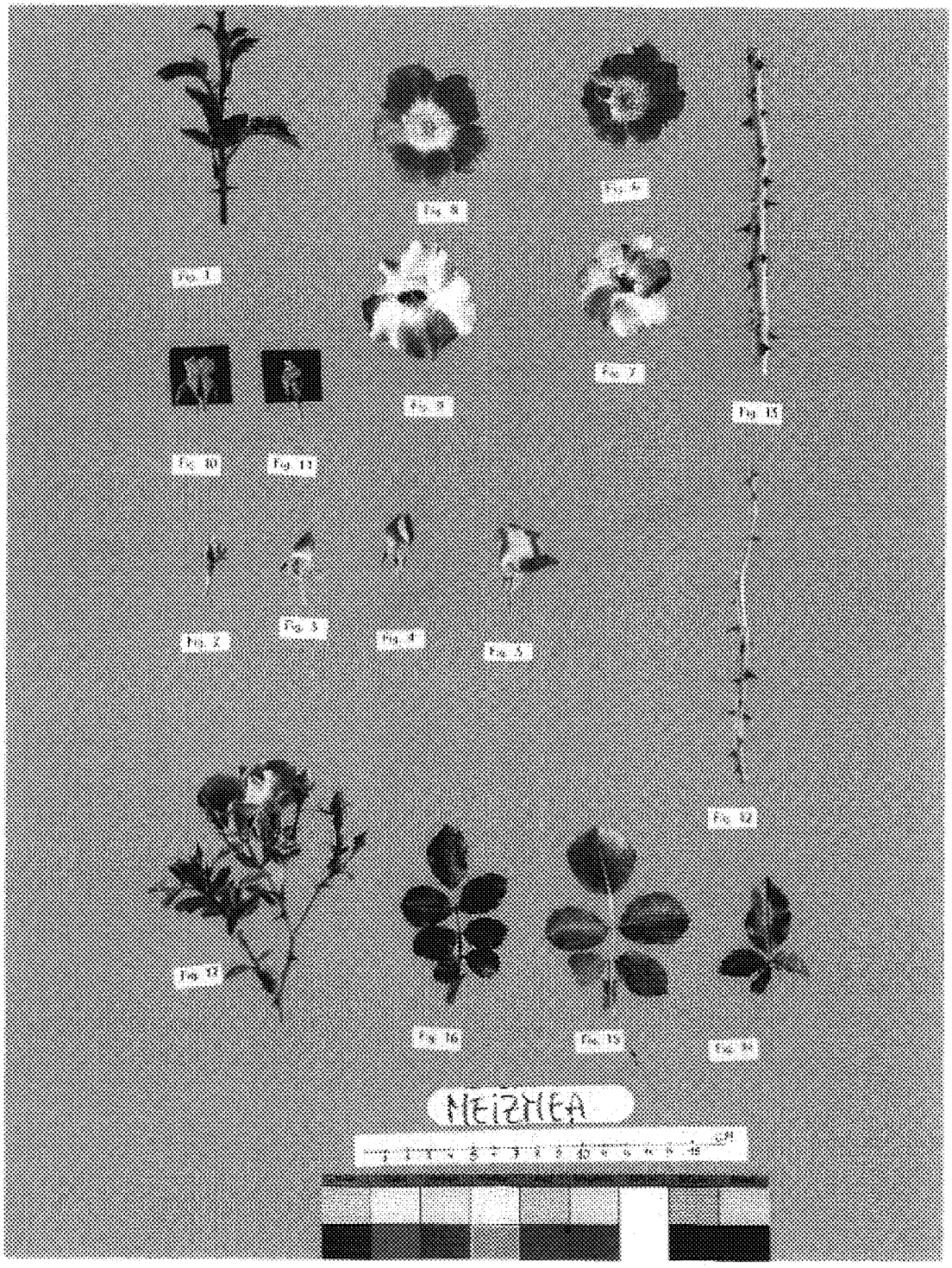

Botanical/commercial classification: *Rosa hybrida*/Shrub Rose Plant.
Varietal denomination: cv. Meizmea.

SUMMARY OF THE INVENTION

The new variety of *Rosa hybrida* shrub rose plant was created by artificial pollination wherein two parents were crossed which previously had been studied in the hope that they would contribute the desired characteristics. The female parent (i.e., the seed parent) was the product of the cross of the 'Kormax' variety (non-patented in the United States) and an unnamed seedling (non-patented in the United States). The male parent (i.e., the pollen parent) was the product of the cross of the 'Meipoque' variety (U.S. Plant Pat. No. 5,956) and the 'Korimro' variety (non-patented in the United States).

('Kormax'×Unnamed Seedling)×('Meipoque'×'Korimro').

The seeds resulting from the above pollination were sown and small plants were obtained which were physically and biologically different from each other. Selective study resulted in the identification of a single plant of the new variety.

It was found that the new Landscape Shrub rose plant of the present invention:

(a) exhibits a bushy and compact growth habit, (b) forms in abundance attractive small single cup-shaped blossoms that are bright red with a light pink center on the upper surface, (c) displays semi-glossy green foliage, (d) exhibits very good tolerance to diseases particularly with respect to Black Spot and Oidium, and (e) is particularly well suited for growing as attractive ornamentation in the landscape.

The new variety well meets the needs of the horticultural industry and can be grown to advantage as attractive ornamentation in parks and gardens.

The new variety can be readily distinguished from its ancestors. The blossoms of the 'Kormax' variety display a generally uniform red coloration. The blossoms of the 'Meipoque' variety display a pink coloration. The blossoms of the 'Korimro' variety display a near white light pink coloration.

The new variety has been found to undergo asexual propagation in France by a number of routes, including budding, grafting, and the use of cuttings. Asexual propagation by the above-mentioned techniques in France has shown that the characteristics of the new variety are stable and are strictly transmissible by such asexual propagation from one generation to another. Accordingly, the new variety can be asexually reproduced in a true-to-type manner.

The new variety has been named 'Meizmea'.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety were approximately one year of age and were observed during June while growing on *Rosa froebelli* understock outdoors at Le Cannet des Maures, Var, France. Dimensions in centimeters and a standard color presentation are indicated at the bottom of the photograph.

FIG. 1—illustrates a specimen of a young shoot;

FIG. 2—illustrates a specimen of a floral bud before the opening of the sepals;

FIG. 3—illustrates a specimen of a floral bud at the opening of the sepals;

FIG. 4—illustrates a specimen of a floral bud at the opening of the petals;

FIG. 5—illustrates a specimen of a flower in the course of opening;

FIG. 6—illustrates a specimen of an open flower-plan view-obverse;

FIG. 7—illustrates a specimen of an open flower-plan view-reverse;

FIG. 8—illustrates a specimen of a fully open flower-plan view-obverse;

FIG. 9—illustrates a specimen of a fully open flower-plan view-reverse;

FIG. 10—illustrates a specimen of a floral receptacle showing the arrangement of the stamens and pistils;

FIG. 11—illustrates a specimen of a floral receptacle showing the arrangement of the pistils (stamens removed);

FIG. 12—illustrates a specimen of a flowering stem;

FIG. 13—illustrates a specimen of a main branch;

FIG. 14—illustrates a specimen of a leaf with three leaflets-plan view-upper surface;

FIG. 15—illustrates a specimen of a leaf with five leaflets-plan view-under surface;

FIG. 16—illustrates a specimen of a leaf with seven leaflets-plan view-upper surface; and FIG. 17—illustrates a cluster of buds in various stages of opening together with one open flower.

DETAILED DESCRIPTION

The chart used in the identification of the colors is that of The Royal Horticultural Society (R.H.S. Colour Chart). The description is based on the observation of one-year-old plants during May while budded on *Rosa froebelli* understock and growing outdoors at Le Cannet des Maures, Var, France.

Class: Landscape Shrub Rose.

Plant:

*Habit.*—Bushy.

Branches:

*Color.*—Young stems: near Green Group 134C. Adult wood: near Green Group 143B.

*Thorns.*—On young stems: Small prickles: quantity: none. Long prickles: Configuration: curved downwards on the upper surface and hooked on the under surface with a narrow and short base. Quantity: approximately 10 on average on a stem length of 10 cm. Length: approximately 0.6 cm on average. Color: near Yellow-Green Group 152B. On adult stems: Small prickles: Configuration: upright and longish pointed on the upper surface and slightly concave on the under surface with a narrow and short base. Quantity: approximately 4 on average on a stem length of 10 cm. Length: approximately 0.3 cm on average. Color: near Greyed-Orange Group 177A. Long prickles: Configuration: upright and longish pointed on the upper surface, and slightly concave on the under surface with a narrow and short base. Quantity: approximately 14 on average on a stem length of 18 cm. Length: approximately 0.8 cm on average. Color: near Greyed-Orange Group 178A.

Leaves:

*Stipules.*—Smooth, adnate, pectinate, broad, approximately 1.4 cm in length on average, approximately 0.7 cm in width on average, near Green Group 137A on the upper surface, and near Yellow-Green Group 147B on the under surface.

*Petioles.*—Upper surface: near Green Group 137C in coloration. Under surface: near Yellow-Green Group 143C in coloration. Texture: non-glandular and with a few prickles on the upper and under surfaces. Length: approximately 2 cm for the terminal leaflet.

*Rachis.*—Upper surface: near Yellow-Green Group 146C in coloration. Under surface: near Green Group 143A in coloration. Texture: smooth.

*Leaflets.*—Number 3, 5 and 7, and most often 3 and 5. Shape: generally oval with a rounded tip and a rounded base. Size: the terminal leaflets commonly are approximately 4.5 cm in length on average. Serration: small and single (as illustrated). Texture: somewhat flexible. General appearance: dense with a semi-glossy aspect. Color (young foliage): Upper surface: near Green Group 139A. Under surface: near Yellow-Green Group 146A. Color (adult foliage): Upper surface: near Green Group 137A. Under surface: near Yellow-Green Group 147B.

Inflorescence:

*Number of flowers.*—Commonly pluriflorous, with a plurality of blossoms per stem.

*Peduncle.*—Smooth, approximately 1.9 cm in length on average, approximately 0.2 cm in diameter on average, and near Green Group 137D in coloration.

*Sepals.*—Upper surface: smooth and near Yellow-Green Group 148B. Under surface: smooth and near Green Group 137C in coloration. Shape: longish and narrow, and tend to be upright at the base. Size: near 2.3 cm in length on average, and near 0.6 cm in width at the widest point on average.

*Buds.*—Shape: elongated. Size: small. Length: approximately 1.5 cm on average. Width: near 1 cm on average at the widest point. Color as the calyx breaks. Upper surface: near Red Group 53A, and amply suffused with Red Group 54A. Under surface: near Red Group 54B, and amply suffused with near Red Group 54A.

*Flower.*—Shape: cup-shaped. Diameter: approximately 2.2 cm on average. Color (in the course of opening): Upper surface: velvety, near Red-Purple Group 61A, and suffused with near Red Group 53A. Under surface: variable, and near Red Group 54C and 54D with some darker red. Spot at base: light pink. Color (when fully open): Upper surface: near Red-Purple Group 57A amply suffused with near Red Group 53A. Under surface: variable, and near Red-Purple Group 62D suffused with near Red Group 55D with some darker red. Spot at base: light pink. Fragrance: none. Petal number: commonly approximately 5 on average under normal growing conditions. Petal shape: with a substantially rounded tip and base. Petal texture: relatively thick. Petal length: approximately 2.9 cm on average. Petal width: approximately 2.9 cm on average. Petal arrangement: imbricated; and commonly with some small petaloids towards the center. Petal drop: good with the petals commonly detaching cleanly before drying. Stamen number: approximately 95 on average. Anthers: regularly arranged around the styles, approximately 0.2 cm in size on average, and near Yellow-Orange Group 17A in coloration. Pollen: present. Filaments: approximately 0.8 cm in length on average and near Yellow Group 3C in coloration. Pistils: approximately 20 on average. Stigmas: approximately 0.2 cm in size on average and near Yellow Group 12C in coloration. Styles: approximately 0.5 cm in length on average, and near Yellow Group 2D in coloration. Receptacle: smooth, funnel-shaped, approximately 0.7 cm in length on average, approximately 0.4 cm in width on average at the widest point, and near Green Group 137C in coloration.

Development:

*Vegetation.*—Strong.

*Blooming.*—Medium season, very abundant, and recurrent.

*Tolerance to diseases.*—Very good, particularly with respect to Black Spot and Oidium.

I claim:

1. A new and distinct Shrub rose plant characterized by the following characteristics:

(a) exhibits a bushy and compact growth habit, (b) forms in abundance attractive small single cup-shaped blossoms that are bright red with a light pink center on the upper surface, (c) displays semi-glossy green foliage, (d) exhibits excellent tolerance to diseases particularly with respect to Black Spot and Oidium, and (e) is particularly well suited for growing as attractive ornamentation in the landscape;

substantially as herein shown and described.

* * * * *

NEIZHEA